United States Patent
Prentice et al.

(10) Patent No.: US 9,217,720 B2
(45) Date of Patent: Dec. 22, 2015

(54) METHOD AND APPARATUS FOR EXTERNAL PIPELINE WELD INSPECTION

(75) Inventors: Garth R. Prentice, Conroe, TX (US); Stephen Knight, Norfolk (GB); Stephen G. Drake, Norfolk (GB)

(73) Assignee: SHAWCOR LTD, Toronto, Ontario (CA)

( * ) Notice: Subject to any disclaimer, the term of this patent is extended or adjusted under 35 U.S.C. 154(b) by 569 days.

(21) Appl. No.: 13/392,672

(22) PCT Filed: Aug. 27, 2010

(86) PCT No.: PCT/GB2010/001622
§ 371 (c)(1),
(2), (4) Date: Apr. 25, 2012

(87) PCT Pub. No.: WO2011/023960
PCT Pub. Date: Mar. 3, 2011

(65) Prior Publication Data
US 2012/0201347 A1    Aug. 9, 2012

(30) Foreign Application Priority Data
Aug. 28, 2009   (GB) .................................. 0915141.6

(51) Int. Cl.
*G01N 23/18*   (2006.01)
*B23K 31/12*   (2006.01)

(52) U.S. Cl.
CPC .............. *G01N 23/18* (2013.01); *B23K 31/125* (2013.01); *G01N 2223/3303* (2013.01); *G01N 2223/3304* (2013.01); *G01N 2223/628* (2013.01); *G01N 2223/629* (2013.01)

(58) Field of Classification Search
CPC .......................... G01N 23/18; G01N 2223/628
USPC .......................... 378/59–60, 197, 57
See application file for complete search history.

(56) References Cited

U.S. PATENT DOCUMENTS 3,445,655 A   5/1969 Curry
3,835,324 A   9/1974 Weigle
(Continued)

FOREIGN PATENT DOCUMENTS

CN   1985147   6/2007
EP   1800114   12/2006
(Continued)

OTHER PUBLICATIONS

Notice of First Office Action (PCT Application in the National Phase), The State Intellectual Property Office of the People's Republic of China, Apr. 1, 2014—English Version.
(Continued)

*Primary Examiner* — Hoon Song
(74) *Attorney, Agent, or Firm* — DeLio, Peterson & Curcio LLC; Kelly M. Nowak

(57) ABSTRACT

An apparatus is provided for external inspection of a pipeline circumferential weld. This comprises a radiation source (5) and radiation detector (3). Both units are controllably movable around a drive band or track (7) which is fitted around the circumferential weld. To align the source with the detector the source and detector are moved with respect to each other clockwise and anticlockwise around an initial position while sampling the radiation detected at a number of positions. A position of maximum strength of the radiation signal detected can then be determined such that the center point of the radiation source may be located. The source and detector are then substantially aligned with each other and means are provided to move the source and detector circumferentially around the weld while remaining substantially in alignment.

20 Claims, 3 Drawing Sheets

(56) References Cited

U.S. PATENT DOCUMENTS

| | | | |
|---|---|---|---|
| 4,078,180 A | | 3/1978 | Green |
| 4,187,425 A | | 2/1980 | Thompson |
| 4,283,629 A | * | 8/1981 | Habermehl et al. ............... 378/4 |
| 4,974,246 A | | 11/1990 | Heiskel |
| 5,014,293 A | | 5/1991 | Boyd et al. |
| 5,388,129 A | | 2/1995 | Hartley |
| 5,698,854 A | | 12/1997 | Gupta |
| 6,466,643 B1 | | 10/2002 | Bueno |
| 6,614,872 B2 | | 9/2003 | Bueno et al. |
| 6,618,465 B2 | | 9/2003 | Mohr et al. |
| 7,027,554 B2 | | 4/2006 | Gaultier et al. |
| 7,108,421 B2 | * | 9/2006 | Gregerson et al. ............ 378/197 |
| 7,656,997 B1 | | 2/2010 | Anjelly |
| 2003/0142783 A1 | | 7/2003 | Daaland et al. |
| 2005/0041775 A1 | | 2/2005 | Batzinger |

FOREIGN PATENT DOCUMENTS

| | | |
|---|---|---|
| EP | 1837644 | 9/2007 |
| GB | 2157930 | 10/1985 |
| GB | 2211708 | 5/1989 |
| JP | 58117445 | 7/1983 |
| JP | 9304303 | 11/1997 |
| JP | 09304303 | 11/1997 |
| RU | 2069854 | 11/1996 |
| RU | 2098796 | 12/1997 |
| RU | 2199109 | 2/2003 |
| WO | WO2006/137905 | 12/2006 |

OTHER PUBLICATIONS

Notice of First Office Action (PCT Application in the National Phase), The State Intellectual Property Office of the People's Republic of China, Apr. 1, 2014—Chinese Version.

Decision to Grant—Application No. 2012110481/28(015716) Filing Date Aug. 27, 2010, Jun. 20, 2014, (English Version).

Decision to Grant—Application No. 2012110481/28(015716) Filing Date Aug. 27, 2010, Jun. 20, 2014, (Russian Version).

* cited by examiner

METHOD AND APPARATUS FOR EXTERNAL PIPELINE WELD INSPECTION

FIELD OF THE INVENTION

This invention relates to a method and apparatus for external inspection of a pipeline weld, such as may be performed using digital real-time x-rays.

BACKGROUND OF THE INVENTION

Pipelines of the type used to transport materials such as gas, oil, etc over long distances are formed of metallic pipeline sections. These are joined together with welds. In most situations, the pipelines are constructed by adding sections sequentially, one section after another. When a section has been added it is welded to the preceding section. Because the end of the newly added section is open, it is possible to inspect the weld from both sides, and this is conventionally done using x-ray penetration of the weld and a suitable detection system such as x-ray sensitive film. In some situations, internal access is difficult to obtain. For example, where a pipeline has to pass beneath a road, the pipeline may be constructed in conventional manner on either side of the road and subsequently a tunnel dug beneath the road through which a pipeline section can be passed which is then connected to the pipeline sections on either side. When this is done, it is often not possible to obtain internal access to the pipeline for inspection of the weld used to connect the pipeline sections. Therefore, a system of inspection completely external to the pipeline has to be provided.

Conventionally, such welds have been inspected by using a high strength, broad beam radioactive source such as x-ray or gamma-ray to penetrate both walls of the pipeline and to expose an x-ray/gamma-ray sensitive film plate on the opposite side of the pipeline to the x-ray/gamma-ray source.

In order to obtain a complete image of the weld a plurality of exposures are required and six or more is not uncommon, dependent upon pipeline diameter. This is to enable the weld to be inspected at all positions around the circumference of the pipeline. The broad beam nature of the source also requires the exposures to be relatively long and the radiation exclusion area which needs to be provided around the x-ray/gamma-ray source is therefore extensive.

SUMMARY OF THE INVENTION

Preferred embodiments of the present invention provide, in their various aspects a method and apparatus for real-time external inspection of the integrity of circumferential welds in pipelines. The need to use an internal x-ray source or broad beam external x-ray or gamma-ray source is eliminated. Embodiments also seek to eliminate the use of x-ray/gamma-ray film plates and the associated chemicals required for their processing.

One aspect of the present invention provides an apparatus for external inspection of a pipeline circumferential weld comprising a radiation source and a radiation detector independently mountable upon opposing external sides of the pipeline weld and independently movable circumferentially around the weld, and means to move the source and the detector with respect to each other clockwise and anticlockwise around an initial position whilst sampling the radiation detected at a number of positions to determine a position of maximum strength of the radiation signal detected, whereby the centre point of the radiation source may be located, and the source and detector substantially aligned with each other, and means for moving the source and detection circumferentially around the weld whilst remaining substantially in alignment detector substantially aligned with each other and mountable upon opposing sides of a pipeline circumferential weld.

DETAILED DESCRIPTION OF PREFERRED EMBODIMENTS

Figure 1:
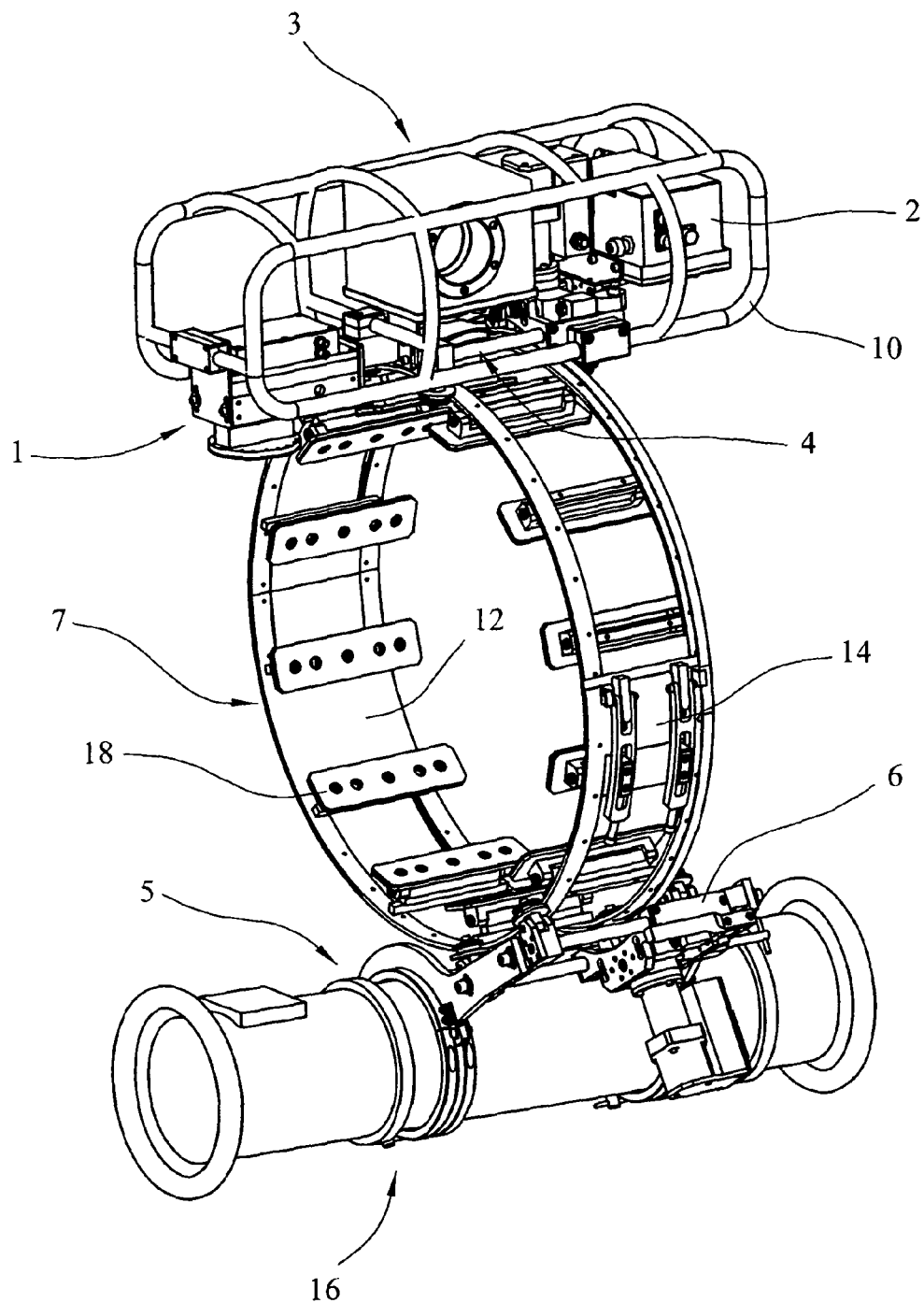
FIG. 1 shows a perspective view of an embodiment of the invention.

The perspective view of an embodiment of the invention in FIG. 1 shows the following elements. An x-ray detection assembly includes an x-ray detection sensor 1 coupled to image collection equipment 2. The x-ray detection sensor 1 and image collection equipment 2 are mounted in a protective tubular frame 10. The x-ray detection assembly 3 is attached to a motorised buggy 4 which is controllably movable around a drive band or track 7. This drive band or track can be clamped around a pipeline whose welds require inspection. Clamping of the track around the pipeline is achieved by providing the track in two portions which are hinge connected at location 12 and are secured around the track 7 by securing devices 14.

Also movably mounted on the track 7 via motorised buggy 6 is an x-ray source assembly 16 comprising an x-ray source 5. The motorised buggies 4 and 6 may be controlled in synchronism to move the x-ray detection assembly and x-ray source assembly around the track to inspect the weld. The x-ray source and the x-ray detector are mounted on their respective assemblies at positions longitudinally spaced along lines parallel to the axis of the external track 7 such that the track is not between the x-ray source and the x-ray detector.

The track is positioned around the pipeline by mounting pads 18 which space the track radially from the pipeline thereby enabling the x-ray detection assembly and x-ray source assembly to be securely mounted on the track via their motorised buggies. The x-ray source and x-ray detector assemblies can then be controllably moved around the track in synchronism to inspect a circumferential weld.

The x-ray detector comprises a highly sensitive x-ray sensor and the image collection equipment 2 comprises a digitiser and serial communication convertor. Preferably the x-ray detector assembly is cooled to a constant temperature to ensure stable operation. This is achieved by the use of cooling fluid passing through the tubular frame 3.

The x-ray detector used has resolution and contrast capabilities which are preferably substantially similar to that of medium speed x-ray film plates. In some applications different sensitivities may be required. The x-ray detector is sufficiently sensitive to be able to collect x-ray quanta several orders better than conventional x-ray film plates are able to detect The X-ray detector is based on a highly customised version of an existing product used in dentistry and designed specifically for low dose, high speed panoramic x-ray. This commercial product scans a patient's jaw at high speed using a multiple line charge coupled device (CCD) which can either directly or indirectly convert low energy x-rays to an electronic signal.

By way of example one commercially available system is made up of a 3072×128 element CCD covering 150 mm width The scan speed of the mechanism that orbits the patients jaw is linked to the charge transfer rate from line to line on the CCD, resulting in a single output signal row with 128 times the amplitude of a single row of detectors. This type of detector is commonly called a 'time division integration' device.

In use the CCD moves around its scanning arc in a direction perpendicular to its 128 rows of CCD elements. Each element is, for example 50 microns in diameter. Charge from the elements in each row is read in a first scan is stored in respective ones of a plurality of registers, one register for each row, and each register including a storage element for each CCD element.

The CCD then advances and a second scan is performed when it has advanced a distance substantially equal to one row of CCD elements (in this case 50 microns). Charge from the elements in each row is read in the second scan. The charge is added to charge already stored for the respective row position in relation to the article being scanned. That is to say, on the first scan the leading row of CCD elements will have its charge stored in a first register, the second row in second register, and so on. On the second scan, the leading row of CCD elements will have its charge stored in a new register. The second row of CCD elements will have its charge added to the charge in the first register as it is now detecting in the same position as the first register was on the first scan. This process of stepping through registers and adding charge to each one each time the CCD elements have moved by one row for a further scan continues until charge from the final row of CCD elements has been written to the first register. When this has happened, data from the first register can be sent to the digitiser and serial communication converter.

After the next scan the register corresponding to the second position of the first row of the CCD elements will be finished accumulating charge and can be sent to the digitiser. This process continues for the whole of the item being scanned. Thus, for each position on the scan, the charge from 128 rows of CCD elements is accumulated into a single register, for each position on the scan, thereby producing a signal where only significant variations will be masked by noise.

The overall system used by the detector described in this embodiment uses the same principles as the commercial dental product described above, but has been adapted in five novel ways.

Firstly the detection width is reduced to 75 mm, which is the usual inspection width for welds. In this example the CCD array is therefore reduced to 1536×128 elements, but other configurations are possible.

Secondly the CCD device is protected against higher energies (typically 300 kV or more) used for girth weld inspection by a deep (typically 50 mm to 100 mm in depth) radiation absorbing coherent fibre optic block covering the CCD input window.

Thirdly the CCD and its electronics are shielded by a heavy metal radiation absorbing housing to reduce scattering of x-rays.

Fourthly the fibre optic block is coupled to a field changeable x-ray scintillator that consists of a polycrystalline x-ray to light convertor, made up of millions of needle like crystals, bonded to a low density carrier plate.

Fifthly the CCD detector and the electronics are cooled via Peltier devices to maintain a low dark current and high stability. This allows the detector to scan the girth weld at slow speeds when required.

The x-ray detector electronics are synchronized to the scanning mechanism via a master clock such that data from the CCD is sampled each time the detector has advanced by one row of CCD elements. The master clock ratios between the mechanical movement of the detector and the detector transfer clocks can be varied in such a manner to 'focus' the x-ray data collection at a particular plane in space. In most applications this is in the centre of the weld, but other operations are possible. The effect of this approach is to focus the wanted lamina data (Laminography) at the area of interest whilst presenting the areas outside this specific plane as out of focus. Using this detector, the system is able to produce data from x-rays which have penetrated through both walls of the pipeline and is still able to deliver sensitivities which are comparable with a film plate taken through a single wall of the pipeline. This is achieved by the increased sensitivity of the detection system and the virtual elimination of the effects of the pipe surface closest to the x-ray source utilising the systems laminar properties.

Figure 3:
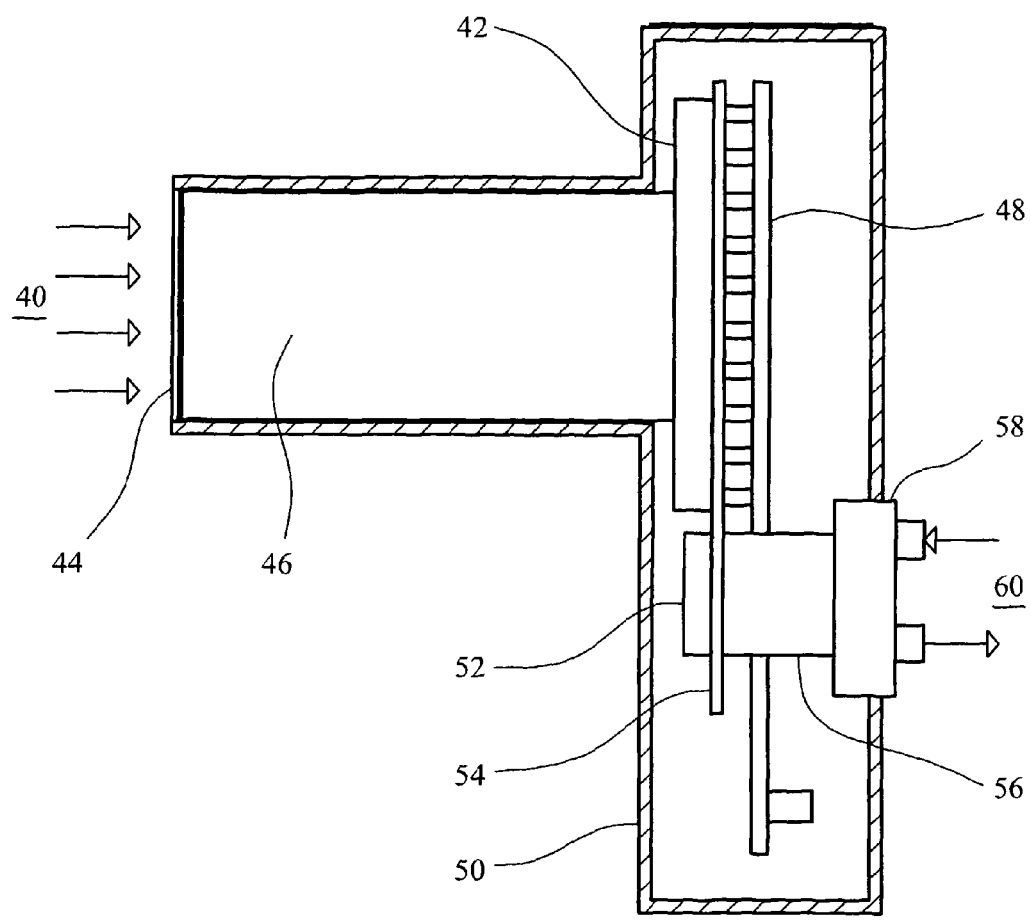
FIG. 3 shows an embodiment of an x-ray detector for use in the system of FIG. 2.

FIG. 3 shows a schematic diagram of the x-ray detector. X-rays 40 enter the assembly. They are converted to light at a wavelength suitably matched to a CCD 42 by a field changeable x-ray scintillator 44 that consists of a polycrystalline x-ray to light converter. This converts the x-rays to light and then passes them to the coherent fibre optic block 46.

The CCD device 42 and the interface electronics 48 are enclosed in a heavy metal radiation absorbent housing 50. Peltier effect devices 52 cool the CC detector 42 via a thermal transfer plate 54 fixed between the back of the CCD and the printed circuit board which bears the interface electronics. Heat is passed via the copper plates 56 to a copper block 58. A liquid coolant is pumped through the copper block via inlet and outlet connections 60. The cooling of the CCD device allows the detector to scan the weld at slow speeds when required and also allows it operate in high ambient temperatures.

The x-ray detector is moved around the circumferential weld at a constant speed by the first buggy 4 which moves around the drive band or track 7. As it moves, x-rays are detected by the x-ray sensor 1 which provides output data to the digitiser and serial communication convertor 2. This in turn is coupled to an external control centre such as a computer which also provides control signals to the motorised buggy to drive the detector around the track and in synchronism with this reads data from the digitiser and serial communication converter 2 as it is connected by the x-ray sensor 1.

At the same time, the x-ray source assembly is controlled by the control centre to move around the track in synchronism with the x-ray detector assembly but on the opposite side of the track speed approximately 180° around the track from the x-ray detector. This ensures that the x-ray source is directed substantially towards the x-ray detector as they both move around the track 7.

The speed at which the detector and its associated electronics transfer data to the control centre are synchronised with the movement of the detector assembly around the track 7 in such a manner as to "focus" the x-ray data collection on a particular plane in space. The use of a CCD device in 'time delayed Integration' mode as discussed above, means that the data set will only be in 'focus' over a narrow range of locations between the x-ray source and the detector. By choosing a mechanical orbiting velocity and a detector row clock that presents the data at the weld surface under inspection in such a manner that it is stationary over all the CCD rows of the detector, any data acquired in other places between the source and detector (i.e. the weld nearest to the x-ray source) will be out of focus. In most applications this is in the centre of the weld but other arrangements are possible. The effect of this is to focus the detection of data at the area of interest, preferably the closest point on the circumferential weld to the detector, whilst presenting other areas outside this as out of focus. Because of the synchronisation of the transfer clocks which send data to the control centre, a set of lamina data is produced as the detector scans around the circumferential weld, i.e. data from the scan is accumulated sequentially as the detector moves, one row at a time, and is sent to the digitiser and then onwards for analysis.

The x-ray source is collimated to a narrow fan beam. This ensures that it is directed substantially at the area of the circumferential weld thereby reducing the scattering of unused x-rays. The two motorised buggies 4 and 6 are controlled by signals from the control centre. They move in synchronism around the track 7. Preferably each has onboard motor drives. They may, however, be coupled together for movement in a master/slave operation.

The buggies are engaged on the drive band or track 7 which allows the motors to drive them around the pipeline circumference. A toothed rack may be fitted to the drive band to engage the buggies to provide smooth and secure scanning of the pipeline's circumference. In another embodiment, the drive band mechanism could be replaced by a hinged 'claw' annulus type rotational device suspended over the pipeline carrying the x-ray source and x-ray detector Cables from the x-ray source assembly and x-ray detector assembly are routed back to the control centre or inspection station which performs control and image capture/storage.

The system scans the entire circumference of a pipeline circumferential weld using a radiographic technique known as Double Wall, Single Image (DWSI). The system is configured via the control centre to produce an x-ray image which appears as a continuous long strip of weld. This is produced from a succession of sample images from the focused x-ray detector. Out of focus data is not used in this. Thus, from an image perspective the image displayed is of a similar type to that which would be collected using a single image (SWSI) arrangement which is used where access to the interior of the pipeline is possible.

Alternatively the x-ray source may be moved clockwise and anticlockwise with respect to the detector, or the source and detector may be moved clockwise and anticlockwise with respect to each other.

To ensure that the x-ray detector is properly aligned with the x-ray source before an x-ray image detection begins, the system is arranged to perform an x-ray search initially. In this, the x-rays are first energised and the x-ray detection system is then controlled to enter an x-ray search mode of operation. In this it orbits about its initial position on the circumferential track 7 in both clockwise and anti-clockwise directions. As it moves, samples of the x-ray data detected are provided to the control centre which determines the minimum and maximum strength of the x-ray signals detected on the arc around which it moves. From this it is able to calculate the position at which the maximum strength of the x-ray signal is detected thereby determining substantially the x-ray beam centre. Once this centre point has been located the x-ray detector assembly is moved to this position without movement of the x-ray source buggy.

The system then moves to scanning mode in which the x-ray detector assembly and x-ray source assembly are both moved around the track in synchronism at the same speed and maintaining the same circumferential displacement selected by the x-ray search mode to perform a scan of a circumferential weld.

Figure 2:
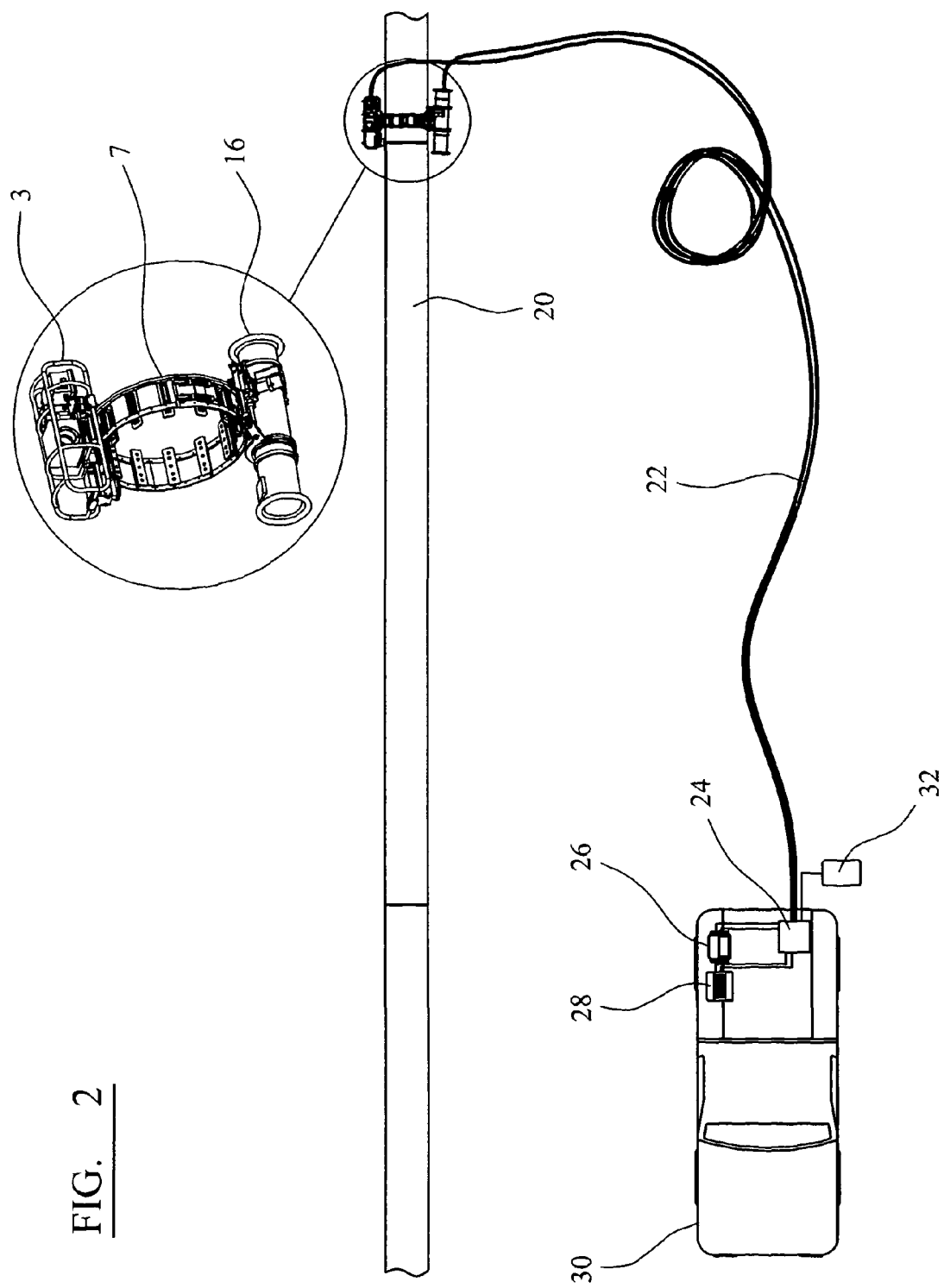
FIG. 2 shows a view of the embodiment of FIG. 1 clamped around a pipeline circumferential weld and coupled to a recording station.

FIG. 2 shows schematically the x-ray inspection system mounted on a pipeline. The drive band or track 7 is clamped to the pipeline circumference 20. The x-ray detector assembly 3 is then clamped to the track 7 and the x-ray source assembly 16 to a position approximately diametrically opposed to the x-ray detector assembly. Control cables 22 are connected to the two assemblies and couple them to a low voltage power source 24, a laptop computer 26, and an x-ray controller 28. These are provided in a vehicle 30 which can be positioned at a safe distance from the x-ray inspection system. A portable generator 32 supplies the complete system with power, although in some embodiments the vehicle could be used as the power supply.

In operation, the system is energised and the x-rays are initially switched on so that the x-ray search mode can be entered to find the centre of the x-ray beam. Once this has been located a full scan of the circumferential weld is performed. The results are then interpreted and saved. The inspection system can then be moved to the next weld to be inspected.

In an alternative embodiment multiple detectors may be provided circumferentially on either side of the detector in the illustrated embodiment on the same orbiting buggy so that they can be moved circumferentially around the weld at the same time as the main detectors.

For example, two additional detectors can be mounted on either side of the main detector on the same orbiting buggy. The width of the x-ray source fan beam may have to be increased to ensure that radiation strikes all three detectors. The processing of the resultant data comprises overlaying the detected radiation data from each additional detector with the data from the main detector for each position which the detectors pass. The detectors will be identical detectors and preferably the CCD devices described above. The data from the three detectors for each position around the circumference is then summed which results in improved signal to noise ratio for the resultant data thereby permitting an increase in orbiting speed in comparison with a single detector.

It will be appreciated that embodiments of the invention can be used to inspect circumferential welds on pipelines where access to the inside of the pipelines is not possible. Another application for embodiments of the invention is the inspection of circumferential welds in small diameter pipelines where the internal diameter is too small to conveniently deploy a radiation source.

This system may also be modified to inspect welds on pipelines and conduits which are not circular.

The invention claimed is:

1. Apparatus for external inspection of a pipeline circumferential weld, comprising:
   a track adapted for clamping around the pipeline;
   an x-ray source assembly and an x-ray detector assembly independently mountable upon the track on opposing external sides of the pipeline weld and independently movable circumferentially around the track, wherein the x-ray detection assembly comprises an x-ray detection sensor coupled to image collection equipment, and wherein the x-ray source assembly comprises an x-ray source;
   means to move the x-ray source assembly and the x-ray detector assembly with respect to each other clockwise and anti-clockwise around an initial position whilst sampling x-ray radiation detected at a number of positions to determine a position of maximum strength of the x-ray radiation signal detected, whereby the centre point of the x-ray source may be located and the x-ray source and the x-ray detector substantially aligned with each other;

wherein the radiation x-ray source is collimated into a narrow fan beam illuminating the x-ray detector and the detector is shielded by a radiation absorbing housing to reduce scattering of the x-ray radiation; and further comprising means for moving the x-ray source assembly and the x-ray detector assembly circumferentially around the weld whilst remaining substantially in alignment, wherein the x-ray detection sensor and the x-ray source are mounted on their respective assemblies at positions longitudinally spaced along lines parallel to an axis of the track, such that the track is not located between the x-ray source and the x-ray detection sensor.

2. Apparatus according to claim 1 in which the x-ray source and the x-ray detector are each carried by respective motorised buggies which are controllably movable around the track.

3. Apparatus according to claim 2 in which the track is detachably mountable around the pipeline circumferential weld.

4. Apparatus according to claim 2, further comprising a plurality of mounting pads adapted to space the track from the pipeline.

5. Apparatus according to claim 2 in which the x-ray source assembly and the x-ray detector assembly are controllably movable in synchronisation around the track.

6. Apparatus according to claim 2 in which the track comprises two portions hingeably connected.

7. Apparatus according to claim 1 in which the radiation x-ray detector is focused on a narrow section of the pipeline circumferential weld, and the x-ray detector reads data from the section of the pipeline circumferential weld on which it is focused as it moves around the weld thereby producing a linear set of detection data relating to the integrity of the weld.

8. Apparatus according to claim 7 in which the x-ray detector comprises an x-ray to light convertor on which the x-ray radiation falls and which transmits light through a radiation absorbing fibre optic block to a charge coupled device (CCD) which detects the intensity of the light.

9. Apparatus according to claim 8 in which the CCD comprises a two-dimensional array of detector elements and the charge sampled by the CCD is sampled in synchronisation, row-by-row with mechanical movement of the CCD over a predetermined number of rows of the array, and charge sampled at each position of each row is accumulated into a plurality of respective registers.

10. Apparatus according to claim 9 in which the resultant signal output from charge accumulation over the CCD device's predetermined number of rows is a single output row, containing the total charge accumulation from the predetermined number of rows chosen for the weld inspection.

11. Apparatus according to claim 1, wherein the image collection equipment comprises a digitiser and a serial communication converter.

12. Apparatus according to claim 1, wherein the x-ray detection assembly and the x-ray source assembly are each mounted on a motorised buggy which is controllably movable around the track.

13. Apparatus according to claim 1, wherein the x-ray detection assembly is mounted in a protective tubular frame.

14. Apparatus according to claim 13, wherein the x-ray detection assembly is cooled by a cooling fluid passing through the tubular frame.

15. Apparatus according to claim 8, wherein the fibre optic block covers an input window of the CCD, and the fibre optic box has a depth of 50-100 mm.

16. Apparatus according to claim 8, wherein the fibre optic block is coupled to a field changeable X-ray scintillator which converts x-rays to light and passes them to the fibre optic block.

17. Apparatus according to claim 8, wherein the CCD and its electronics are shielded by a heavy metal radiation absorbing housing.

18. Apparatus according to claim 8, wherein the CCD and its electronics are cooled by Peltier devices.

19. Apparatus for external inspection of a pipeline circumferential weld, comprising:

a track for clamping circumferentially around the pipeline having a track interior surface and a track exterior surface, when the track is clamped around the pipeline the track interior surface faces toward the pipeline and the track exterior surface faces away from the pipeline;

an x-ray detection sensor and an x-ray source each independently mounted on the track exterior surface on opposing sides of the track, the x-ray source and the x-ray detection sensor are each mounted parallel with the track exterior surface and parallel with the pipeline and are independently movable circumferentially around the track exterior surface;

a plurality of mounting pads attached only to the track interior surface to space the track radially apart from the pipeline and to allow the x-ray detection sensor and the x-ray source to be securely mounted on the track exterior surface;

means to move the x-ray source and the x-ray detection sensor with respect to each other clockwise and anti-clockwise around an initial position while sampling x-ray radiation detected at a number of positions to determine a position of maximum strength of the x-ray radiation signal detected, whereby the center point of the x-ray source may be located and the x-ray source and the x-ray detection sensor substantially aligned with each other;

wherein the radiation x-ray source is collimated into a narrow fan beam illuminating the x-ray detection sensor and the detector is shielded by a radiation absorbing housing to reduce scattering of the x-ray radiation; and wherein the x-ray detection sensor and the x-ray source reside a distance above the track, such that the track is not located between the x-ray source and the x-ray detection sensor.

20. Apparatus for external inspection of a pipeline circumferential weld, comprising:

a track having a track interior surface, a track exterior surface and track upper and lower surfaces, the track detachably clamps circumferentially around the pipeline whereby the track interior surface faces toward the pipeline and the track exterior surface faces away from the pipeline;

an x-ray source assembly on a first motorized buggy and an x-ray detector assembly on a second motorized buggy each independently mounted on the track exterior surface on opposing sides of the track, the x-ray source assembly and the x-ray detection assembly are each mounted parallel with the track exterior surface and parallel with the pipeline and are independently movable circumferentially around the track exterior surface via the first and second motorized buggies, the x-ray source assembly includes an x-ray source and the x-ray detection assembly includes an x-ray detection sensor coupled to image collection equipment;

a plurality of mounting pads attached only to the track interior surface to space the track radially apart from the pipeline and to allow the x-ray detection sensor and the x-ray source to be securely mounted on the track exterior surface via the first and second motorized buggies, the first and second motorized buggies attaching to the upper and lower surfaces of the track and residing on the track exterior surface;

means to move the x-ray source assembly and the x-ray detector assembly with respect to each other clockwise and anti-clockwise around an initial position while sampling x-ray radiation detected at a number of positions to determine a position of maximum strength of the x-ray radiation signal detected, whereby the center point of the x-ray source may be located and the x-ray source assembly and the x-ray detection assembly substantially aligned with each other;

wherein the radiation x-ray source is collimated into a narrow fan beam illuminating the x-ray detector and the detector is shielded by a radiation absorbing housing to reduce scattering of the x-ray radiation; and further comprising means for moving the x-ray source assembly and the x-ray detector assembly circumferentially around the pipeline whilst remaining substantially in alignment, wherein the x-ray detection sensor and the x-ray source are mounted on their respective assemblies at positions longitudinally spaced away from the track, such that the track is not located between the x-ray source and the x-ray detection sensor.

* * * * *